United States Patent [19]

Banks

[11] Patent Number: 5,382,331
[45] Date of Patent: Jan. 17, 1995

[54] METHOD AND APPARATUS FOR INLINE ELECTROCHEMICAL MONITORING AND AUTOMATED CONTROL OF OXIDIZING OR REDUCING AGENTS IN WATER SYSTEMS

[75] Inventor: Rodney H. Banks, Naperville, Ill.

[73] Assignee: Nalco Chemical Company, Naperville, Ill.

[21] Appl. No.: 97,654

[22] Filed: Jul. 26, 1993

[51] Int. Cl.$^6$ ............................................. G01N 27/26
[52] U.S. Cl. ............................... 204/153.14; 204/409; 204/406; 204/407; 204/408; 204/402; 204/153.11; 204/153.22
[58] Field of Search ............... 204/402, 406, 407, 408, 204/409, 412, 153.11, 153.14, 153.22, 232, 267, 269

[56] References Cited

U.S. PATENT DOCUMENTS

| | | | |
|---|---|---|---|
| 4,033,830 | 7/1977 | Fletcher, III | 204/408 |
| 4,566,949 | 1/1986 | Berger | 204/402 |
| 4,668,346 | 5/1987 | Entwistle | 204/402 |
| 4,822,474 | 4/1989 | Corrado | 204/402 |

OTHER PUBLICATIONS

Literature Search Report, Search No. 3367, Nalco Chemical Company.
Literature Search Report, Search No. 4314, Nalco Chemical Company.
TaKung Chen, Yau Yi Lau, Danny K. Y. Wong, and Andrew G. Ewing, "Pulse Voltammetry in Single Cells Using Platinum Microelectrodes," American Chemical Society, 1992.
Edison Sensor Technology Center, Case Western Reserve University, "Chemical Ion Sensors," Jun. 1989.
James A. Cox and Pawel J. Kulesza, "A Selective Eldctrolytic Sensor for Nitrite Base on a Modified Platinum Electrode," Elsevier Science Publishers, B.V., 1984.
J. E. Harrar, "Determination of Nitrite by Controlled-Potential Coulometry," Analytical Chemistry, vol. 43, No. 1, Jan., 1971.

*Primary Examiner*—John Niebling
*Assistant Examiner*—Bruce F. Bell
*Attorney, Agent, or Firm*—Lloyd L. Zickert; Robert A. Miller

[57] ABSTRACT

Method and apparatus for electrochemical monitoring of oxidizing agents, such as nitrite, or reducing agents in a water system and for controlling concentration levels for protecting surfaces exposed to the water. The apparatus includes a probe for selective exposure to fresh water samples of the system. The probe is connected to an analyzer that operates the probe and measures agent concentration by a chronoamperometry technique. A controller selectively feeds an agent to the water system in accordance with a set point to maintain a desired concentration level.

40 Claims, 5 Drawing Sheets

METHOD AND APPARATUS FOR INLINE ELECTROCHEMICAL MONITORING AND AUTOMATED CONTROL OF OXIDIZING OR REDUCING AGENTS IN WATER SYSTEMS

DESCRIPTION

This invention relates in general to a method and apparatus for inline electrochemical monitoring of an oxidizing or reducing agent in a water system, and more particularly to a method and apparatus for inline electrochemical monitoring and automated control of nitrite in a closed cooling system.

BACKGROUND OF THE INVENTION

Commercial water systems generally rely on the use of steel components for transporting water. Accordingly, a major concern in the operation of such systems is the control of steel corrosion. Steel surfaces exposed to water eventually form a protective oxide film that reduces the rate of metal corrosion. However, since oxide formation is relatively slow, severe pitting of a fresh surface can occur. Further, bare metal surfaces are continually forming on mechanical components such as pump pistons and pump impellers that move rapidly or suddenly. At these surfaces small gas bubbles develop and then violently collapse causing destruction of the oxide film. During the time when the oxide layer re-forms, cavitation corrosion (pitting) can occur.

The value of nitrite ($NO_2$) as a cooling system corrosion inhibitor for steel is well recognized because nitrite increases the rate of iron oxide formation on fresh steel surfaces. This is particularly important for protecting mechanical parts whose oxide layers are constantly being stripped away. It is therefore desirable to always maintain proper nitrite levels in a cooling system being treated with a nitrite inhibitor.

There are three common problems associated with maintaining proper treatment levels in a closed cooling system. First, improper maintenance of system treatment levels is often encountered due to neglect. Closed systems are often assumed to be self-sufficient, resulting in infrequent inhibitor level checks by operators. Also, system leaks reduce nitrite treatment levels forcing operators to quickly apply corrections. Secondly, where bacterial infestation is encountered, nitrite is consumed as a food source, thereby reducing active nitrite level. A low nitrite level can falsely indicate low product feed rate. Increasing feed rate without biocide control would only further nourish the bacteria causing them to further multiply. Thus, the pH of the cooling water must also be monitored at times to obtain information on bacterial content. Thirdly, uncontrolled water loss such as leaks reduce nitrite treatment levels forcing the operator to quickly apply corrections. This may result in inconsistent production or system operation.

Since nitrite is continually being consumed both as a corrosion inhibitor and as a bacterial food source, inert tracers cannot be used reliably to control product level. Nitrite itself must be monitored.

An example of a closed cooling system is water cooling rollers in a continuous steel casting machine where water is circulated under pressure between a heat exchanger and the rollers. To control corrosion in such a closed system, a nitrite-containing compound is employed as a corrosion inhibitor, although other corrosion inhibitors may be used. Knowing the significant parameters in a system, such as water quality, water usage rate, and system metallurgy, the standard concentration for nitrite to inhibit corrosion can be determined.

Heretofore, it has been known to analyze nitrite concentration within a closed water cooling system with a titrimetric analyzer. More specifically, a field programmable analyzer (Model 301) made by Tytronics, Inc. has been programmed and slightly modified to analyze for nitrite in a closed water cooling system. The titrator was modified to produce an output signal referenced against a set point to control the operation of a feed pump and the feeding of nitrite to the cooling system. Operation of the titrator requires administration of a reagent for oxidizing nitrite. An oxidation-reduction-potential (ORP) electrode measures the potential in the testing cell. At a certain value, corresponding to the titration end point, the volume of titrant added is proportional to the analyte concentration. If the measurement is below a set point, the feed pump is energized to feed nitrite to the cooling system. This mode continues until a further measurement is taken which detects the concentration level to be above the set point, thereby causing the feed pump to be de-energized. Thereafter, when a further measurement is taken indicating the concentration level to be below the set point, the feed pump is again energized to feed nitrite into the cooling system.

This titrimetric technique of measuring nitrite concentration requires a cell construction providing a well defined sample volume. The analysis times are rather long and, of course, a reagent is necessary in order to perform a titration. Further, the commercial titrator is very costly and requires frequent maintenance.

SUMMARY OF THE INVENTION

The method and apparatus of the present invention electrochemically monitors the concentration of an oxidizing or reducing agent used in a commercial water system and particularly overcomes the difficulties previously encountered in prior monitoring and control systems. The present invention is particularly useful to monitor and automatically control nitrite levels in closed water cooling systems, although it may be used for monitoring and controlling oxidizing agents such as biocides and other corrosion inhibitors or reducing agents such as oxygen scavengers. Moreover, the invention may be employed solely for monitoring chemical concentration in an installation, or for monitoring concentration where manual addition of an agent is contemplated.

The method and apparatus of the present invention is substantially less costly to manufacture and operate over the titration apparatuses of the prior art. Moreover, the present invention does not require the use of reagents and is capable of providing concentration measurements quickly within a few seconds and independently of the size of sample. Cost of the apparatus of the present invention is substantially less than the titrimetric apparatus heretofore used and on the order of less than one-tenth of the cost. Maintenance costs are also lower.

The apparatus of the present invention includes a probe adapted to be in contact with a water sample for measuring chemical concentration. The probe includes a plurality of cells, each of which includes a working electrode, a counter electrode and a reference electrode. The electrodes are placed in contact with the sample and driven by an analyzer to conduct periodic measurements of nitrite concentration. Inasmuch as fouling can be a problem with respect to the electrodes of the probe that would prevent accurate measurements, the probe is driven in a cleaning mode except when system checks are made and a measurement is to be taken. For example, in a closed water cooling system for a continuous caster which would involve circulation of millions of gallons of water and the use of nitrite to inhibit corrosion, the analyzer would drive the probe to take a measurement of nitrite concentration at about five-minute intervals. The analyzer would drive the probe in a cleaning mode for about four minutes of the cycle and then conduct system checks before making a measurement. The system checks would include temperature, reference, conductivity, power supply and relationship of one check to another. Thus, the probe is always kept in a cleaning mode except when making system checks and measuring the nitrite concentration.

The probe preferably includes at least two measuring cells. Where the probe includes two cells, each cell would include a working electrode, a counter electrode and a reference electrode. A current measurement is taken at a ramped up voltage stage for each cell and then averaged to provide a more reliable readout for controlling nitrite feeding. A set point is first established in accordance with a desired nitrite concentration. Where automated control of nitrite level is desired, an apparatus is provided to selectively add nitrite to a system. When the nitrite measurement is below the set point, a feed pump is turned on to feed nitrite into the closed water cooling system. The feed pump is maintained in the "on" mode until a subsequent measurement reading is taken which is above the set point. At that time, the pump is turned off and maintained in the "off" mode until a subsequent measurement is taken which is again below the set point. The set point may have low and high values, such as 200/250 ppm.

Where the closed water cooling system involves millions of gallons of circulating water, it has been found satisfactory to take a measurement about every five minutes in order to maintain the nitrite concentration within a desired range. However, for any given system, the measurement period may be increased or decreased.

The analyzer compensates for conductivity and temperature as well as detecting the relation between conductivity, temperature and nitrite measurement. This relation must be reasonable in order to provide an accurate readout. For example, if the conductivity measurement is too low relative to nitrite level or zero because of the absence of a sample, the system will not work properly, and an error message will appear on the display of the analyzer. For example, if the nitrite measurement was 100 ppm, and the conductivity measurement was 100 $\mu S$ (microsiemens), the analyzer would detect an impossible relationship and display an error. Thus, no nitrite level measurement would be taken. A more proper relation between nitrite concentration and the conductivity measurement would be where the nitrite is measured at 110 ppm and the conductivity is measured at 1000 $\mu S$.

The heretofore commercial process titrator used on a closed recirculating cooling system for a continuous steel caster plant required the withdrawing of a sample from the process and filling a cell with a known volume. A mechanical pump metered a titrant solution into the cell until a preset potential is reached as measured by an ORP electrode. It was found that after a short time period in service, periodic maintenance and inspection were required to maintain proper instrumentation. Particular troublesome areas were the pump head and reference electrode junction.

The present invention utilizes a chronoamperometry technique and involves an electrochemical method for determining nitrite concentration that does not use any reagents or expensive equipment with moving parts. Nitrite is oxidized electrochemically in the cooling water matrices for which the measured current is proportional to the nitrite concentration.

The method of measuring the nitrite concentration includes mounting a multi-cell probe in a tee of a line coming from the main recirculating line of the system to carry a sample of the system water to the probe. System water is flushed over the probe head so that a fresh sample is presented to the probe. The water flow over the probe is stopped, thereby statically conditioning the sample for the measurement. Reference and conductivity checks are first taken which, if acceptable, permit the measurement step to be made. The reference check measures the voltage between reference electrodes, and the conductivity check measures current flow in a cell. If the reference check made does not give zero, then an error would result so no measurement is made. The conductivity check is made to make sure that a liquid is present for measurement and also to compensate for conductivity. During the measuring step, the voltage of one cell is ramped up and held for three seconds. Just prior to dropping the voltage, the current measurement of the cell is taken. The cells are switched and the second cell is operated in the same manner as the first cell to take a current measurement. Each cell has its own compensation for temperature and conductivity. The current measurement of each cell is converted into a nitrite concentration or level and then averaged. If the measurement reading is below the set point of desired nitrite concentration, the feed pump is turned on to feed nitrite to the water cooling system. The pump is maintained in an "on" mode until a subsequent measurement is taken. If the measurement is similarly below the set point, the pump will remain in the "on" mode. If the subsequent measurement is above the set point, the pump will be turned off and maintained in the "off" position until a subsequent measurement is taken which falls below the set point.

It is therefore an object of the present invention to provide a new and improved method and apparatus for monitoring the concentration of an oxidizing or reducing agent in a water system, wherein the apparatus has no moving parts and operates on the chronoamperometry technique.

Another object of the present invention is to provide a unique probe for electrochemically monitoring the nitrite concentration in a water cooling system which includes a plurality of cells providing sensor redundancy and which when operated provides in situ probe cleaning and reliability checking together with temperature and conductivity compensation.

A further object of the present invention is in the provision of a method and apparatus for inline electrochemical monitoring and automated control of nitrite in a water cooling system which includes a multi-cell probe, an analyzer for driving the probe and means for selectively adding nitrite to the system.

A still further object of the present invention is to provide a new and improved method for electrochemically monitoring the level of nitrite in a closed water cooling system having a high degree of reliability with minimal maintenance.

Another object of the present invention is to provide a new and improved method for electrochemically monitoring and automatically controlling the level of nitrite in a closed water cooling system.

Other objects, features and advantages of the invention will be apparent from the following detailed disclosure, taken in conjunction with the accompanying sheets of drawings, wherein like reference numerals refer to like parts.

DESCRIPTION OF THE INVENTION

The present invention is a method and apparatus for determining the concentration or level of nitrite in a closed water cooling system and controlling that nitrite level in accordance with a predetermined set point. The apparatus comprises a solid state electrode probe and electronics for providing an output signal proportional to the nitrite level and analyzing the nitrite level relative to the set point and controlling the feed of additional nitrite to the water cooling system. The probe in the form illustrated consists of four electrodes defining a pair of cells and a temperature sensor housed in a suitable support. The electronics include a microprocessor system and components to enable analysis, electrode cleaning, temperature and conductivity compensation, and analog output. Solenoid and pump drivers are operated by the microprocessor to control a solenoid valve and a nitrite feed pump.

The apparatus does not include any moving parts unlike on-line titrators that use pumps and reagents. Titration is a very common technique heretofore known for measuring concentrations of chemicals in a water system.

One specific application of the present invention is to a closed cooling system for a continuous casting machine in a steel mill where it is important to control corrosion on all fresh metal parts. It is well known that nitrite will accelerate oxidation of the fresh metal parts to protect against further corrosion. However, the present apparatus may be used for monitoring concentration of other oxidizing agents and reducing agents in both open and closed water systems. Moreover, the method and apparatus of the present invention has a higher reliability than on-line titrators that use chemical reagents and mechanical pumps and withdraw samples from the system. In this respect, the present invention utilizes an inline probe which eliminates potential sources for operation failure.

The analyzer of the present invention is unique in that it offers sensor redundancy, in situ probe cleaning and reliability checking, and temperature and conductivity compensation. The use of a microprocessor makes the analyzer totally automated.

The probe of the present invention utilizes a pair of glassy carbon or noble metal electrodes that alternately function as working and counter electrodes and a pair of reference electrodes which are silver with a coating of silver chloride or a coating of a mixture of silver chloride and silver sulphide. The ends of the electrodes are exposed to the water sample. These four electrodes define a pair of cells which each operate to take a measurement of chemical concentration to be averaged for producing greater reliability. While the apparatus illustrated includes only a pair of cells, it may be appreciated that it could include additional cells which, when operated, would have their measurements averaged. It has been found that a pair of cells provide adequate measurements for properly controlling the nitrite concentration.

The glassy carbon electrodes are continuously in a cleaning mode except when making measurements. It is important to maintain the electrodes in a clean condition so they do not become excessively fouled and require shutdown and removal for cleaning and also to obtain accurate measurements.

The apparatus would be programmed to take periodic measurements of the nitrite level. For example, in a closed cooling system for a steel casting machine which would involve the circulation of millions of gallons of water, a measurement every five minutes would be adequate to maintain the nitrite level within a desired range. However, the present apparatus could be programmed for other measurement intervals depending upon the system. Where a measurement is taken about every five minutes, the probe would be maintained in a cleaning mode to assure the best possible operation of the glassy carbon electrodes until system checks and a measurement are taken.

The probe is situated in a sample line coming directly off the recirculating line of the water cooling system to continuously provide a sample of the water in the system. A solenoid or otherwise remotely operated valve is provided to hold a fresh sample of water statically in the sample line for a measurement and to flush the sample line prior to a measurement cycle. A feed pump is connected to a supply of nitrite, such as a sodium nitrite product sold by Nalco Chemical Company of Naperville, Ill., for the purpose of controlling corrosion of steel surfaces and the main line of the cooling system. An acceptable set point for maintaining adequate nitrite concentration would have a lower control limit of 200 ppm and a high or upper limit of 250 ppm. When the concentration measured is below 200, the feed pump would be turned on and maintained in the "on" mode until a subsequent measurement is taken, which would show the nitrite level is above 250 ppm. At that point, the feed pump would be turned off and retained in the "off" mode until the concentration goes below 200 ppm. It would be the object of plant personnel to adjust the set point in accordance with the corrosion rate experienced in the system such that the nitrite concentration would be such as to obtain the lowest possible corrosion rate. Because the present invention would closely control the nitrite concentration, it would avoid both excessive and inadequate levels to produce the highest efficiency and optimum results as well as the most economical usage of the nitrite product for controlling corrosion.

To begin an analyzing cycle, the solenoid valve is turned on to flush the sample line and provide a fresh sample. During this time each cell goes through a cleaning cycle. The solenoid valve is turned off to stop the flow of water and provide a static sample for analysis. The power supply is checked by the analyzer to determine if it is correct or within a desired range. A conductivity measurement is taken between the glassy carbon electrodes. A reference electrode check is made between the reference electrodes which are the chloride-coated silver electrodes. A temperature measurement is taken from the temperature compensation sensor in the probe. In the event any of the checks are not within the desired range, an error will show on the display and no nitrite measurement will be taken. Further, in the event that the conductivity check is outside the window of acceptability, the glassy electrodes are subjected to a gas evolution cleaning before proceeding to make the reference electrode check. Such a cleaning is also considered to be a hydrogen blast where a potential is provided between the casing of the probe and the glassy carbon electrodes to produce a hydrogen blast for cleaning the glassy carbon electrodes. The casing provides a much greater surface as the working electrode, which increases the rate of gas evolution. This step serves to remove physisorbed debris from the glassy carbon electrodes.

Assuming the checks on the power supply, cell conductivity, the reference electrodes, and the temperature are within acceptable ranges, the first cell of the probe is conditioned to measure nitrite concentration. This is accomplished by increasing the voltage between one of the glassy carbon electrodes operating as a working electrode and its adjacent reference electrode to oxidize the nitrite for measuring the current flow through the counter and working electrodes which would be proportional to the nitrite concentration. Thus, the nitrite is oxidized electrochemically in the water matrices. Following the analysis by the first cell, the solenoid valve is again turned on to flush the sample line, then both cells are subjected again to cleaning modes, followed by turning off the solenoid valve to provide a static sample for measuring the nitrite concentration at the second cell.

Following the current measurement of the second cell, the analyzer conducts calculations by taking into consideration the conductivity measurement check and the temperature measurement check and then calculating the nitrite level for each cell based on calibration curves that are in memory. The calculations of the nitrite levels are then averaged, after which the display is updated to show the level of the nitrite, the temperature measurement, and the conductivity measurement. Depending upon the set point, a signal may be transmitted to the pump driver to turn the pump on or off. At the display, an indicator light when energized will indicate whether the pump is in the "on" mode. When the light is de-energized, it will indicate the pump is in the "off" mode. Thereafter, the solenoid valve is again turned on to flush the measured sample during which time each of the cells goes through a cleaning mode, after which the solenoid valve is turned off until the next measurement cycle is to be taken. And, as above noted, during that off period, the glassy electrodes are continuously subjected to cleaning.

Further, as above indicated, an occasional physical cleaning of the probe is performed and particularly the glassy carbon electrodes where the probe body or casing is grounded and a potential is applied to the glassy electrodes to produce a hydrogen gas evolution that removes physically attached debris. As above explained, the physical cleaning of the glassy carbon electrodes would also be done if the conductivity check is unacceptable. It will be understood that the cleaning process is an electrochemical cleaning where hydrogen bubbles are generated at the ends of the glassy carbon electrodes which cause agitation to scrub and clean the end surfaces of the electrodes. Because physically attached debris will not clean electrochemically, it is necessary to blow off the electrode surfaces of the glassy carbon electrodes at least once a day or as often as needed by generating a larger current where the casing of the probe that provides a greater area can serve as a working electrode while the glassy carbon electrodes can serve as the counter electrodes in order to generate a large current and vigorous hydrogen evolution at the counter electrode. By making the casing the working electrode, greater quantities of hydrogen gas can be generated to blow off the glassy carbon electrodes and effect a physical cleaning.

Figure 1:
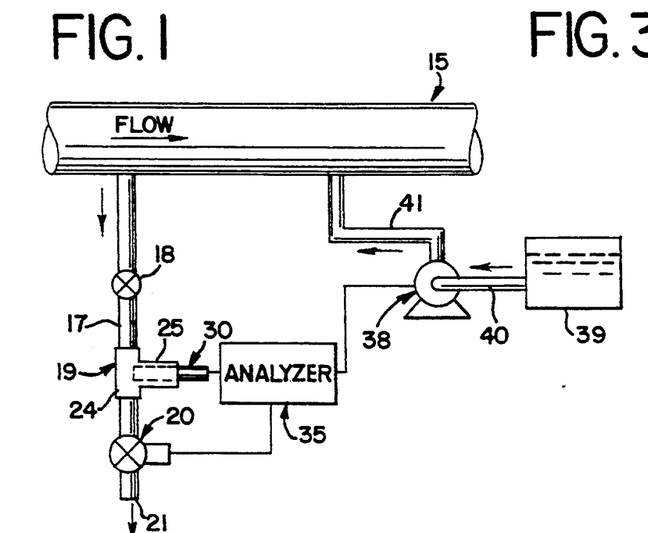
FIG. 1 is a diagrammatic view of a water cooling system line including the chemical concentration level monitoring and controlling apparatus of the present invention.

Referring now to the drawings, and particularly to FIG. 1, the apparatus of the invention for monitoring and controlling the level of nitrite in a cooling system is diagrammatically illustrated with a cooling system recirculating line, generally designated by the numeral 15, through which the water recirculates between heat exchangers and the equipment to be cooled. A sample line 17 is connected to the recirculating line 15 and includes a manual on/off valve 18, a tee fitting 19, and a solenoid-operated valve 20 ahead of a drain 21. It should be appreciated the apparatus of the invention may be used for monitoring and controlling chemical levels in other than cooling systems. It should be appreciated that a pneumatically operated valve or other remotely operable valve may be provided in place of the solenoid operated valve which would operate in response to an electrical signal.

The tee fitting includes a straight-through section 24 connected at opposite ends to the sample line 17 and a tubular section 25 extending at right angles to the straight section 24 with a threaded inlet end 26 into which is threadedly received the probe 30 of the present invention. The probe 30 is shown in more detail in FIGS. 2 to 4.

The apparatus of the present invention includes an analyzer 35, the probe 30 constituting the sensor for the analyzer to sense the concentration level of the nitrite in the sample line. Additionally, the analyzer has an output to the solenoid valve 20 to control operation of the solenoid valve and an output to a nitrite feed pump 38 for controlling the feed of nitrite to the cooling system. The nitrite feed pump includes an inlet connected to a supply or source 39 of nitrite through an inlet line 40 and an outlet or feed line 41 connecting the outlet of the feed pump to the recirculating line 15 of the water cooling system. When the analyzer determines the cooling water needs additional nitrite to maintain the desired concentration, a signal will be sent to turn on the nitrite feed pump and add nitrite to the cooling water. Likewise, when the analyzer determines that the level exceeds a certain set point, it will turn off the feed pump. Further, the analyzer will drive the probe 30 and the solenoid valve 20 in accordance with the program procedures for measuring the nitrite level in the cooling water. While the present invention is shown and described as an automated chemical monitoring and controlling apparatus for a water cooling system, it may be used in the form of a chemical concentration monitoring apparatus where manual feeding of a chemical product may be done by an operator, or the monitoring apparatus may be used strictly for informational purposes.

Figure 2:
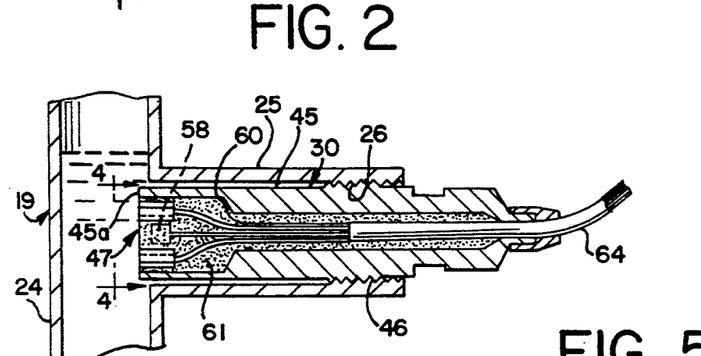
FIG. 2 is an enlarged longitudinal sectional view of the probe of the present invention mounted in a tee fitting on a water sample line.

The probe 30 includes a casing 45 of a suitable metal such as stainless steel. The casing is in the form of an elongated cylinder having external threads 46 at one end to mate with the internal threads 26 of the tee fitting 19 when the probe is properly mounted in the tee fitting. The probe 30 includes a head 47 that will be suitably positioned in the tee fitting to be exposed to the water in the sample line, such as illustrated in FIG. 2. Thus, the head is situated slightly into the internal cavity of the straight section 24.

The casing 45 is hollow to receive and support the electrodes and the temperature compensator and for purposes of extending conductors from these elements through the casing and out the conductor end of the casing. At the head end of the probe, it is hollowed out to receive glassy carbon electrodes 50 and 51, silver electrodes 54 and 55, and a temperature compensation sensor 58, such as an AD590KH component. A single conductor is connected to each of the electrodes, while a pair of conductors is connected to the temperature sensor. Further, a conductor is suitably soldered or welded to the interior of the casing at 60 in the form of a ground for the casing. While glassy carbon electrodes are preferable, electrodes 50 and 51 may be of noble metal, such as gold or platinum, or of any other suitable non-reactive, electrically conductive material. As above noted, the silver electrodes 54 and 55 have an outer end coating of silver chloride, or a coating of a mixture of silver sulphide and silver chloride for sensing chloride. The glassy carbon electrodes and the silver electrodes, together with the temperature compensating sensor, are embedded in an epoxy potting material 61 which supports the electrodes in the sensor in proper position with respect to each other. The outer ends of the electrodes are flush with the outer end of the casing, as noted in FIGS. 2 and 3.

Figure 3:
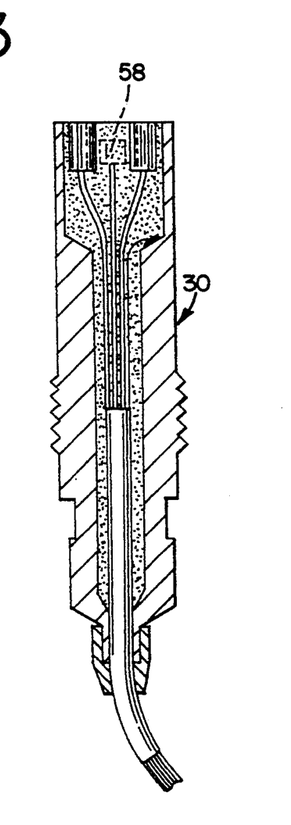
FIG. 3 is a greatly enlarged longitudinal sectional view of the probe employed in the monitoring and controlling apparatus of the present invention removed from the tee fitting.
Figure 4:
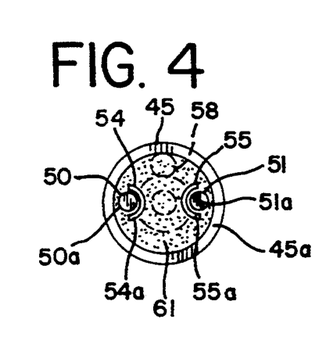
FIG. 4 is a plan view of the working end of the probe shown in FIGS. 2 and 3 showing the electrodes and the temperature sensor in phantom.

The glassy carbon electrodes are spaced from each other along a diameter and also inward of the casing end surface 45a. The glassy carbon electrodes are cylindrically shaped and respectively provided with circular end faces 50a and 51a at the head end of the probe. The silver electrodes 54 and 55 are in the form of half-moon segments or semi-tubular segments with outer or end contact surfaces 54a and 55a. They are spaced in opposing relation and formed to be sized substantially concentric and uniformly spaced to the cylindrical glassy carbon electrodes, the electrode 54 being associated with carbon electrode 50 and the electrode 55 being associated with the carbon electrode 51. Thus, the electrode surfaces 50a, 51a, 54a, and 55a are flush with the casing surface 45a. When the probe is conditioned to physically clean the glassy carbon electrodes, the casing surface 45a acts as the working electrode.

Figure 5:
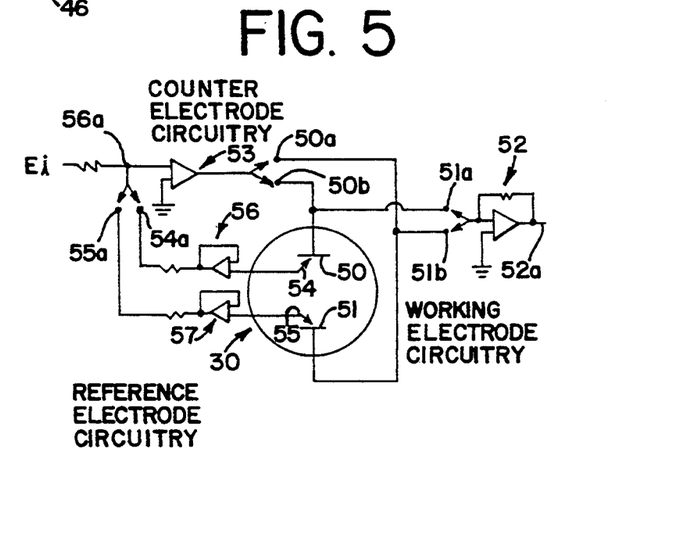
FIG. 5 is an electrical schematic diagram for the probe of the present invention.

The glassy carbon electrodes 50 and 51 alternately function as working and counter electrodes, while the silver electrodes 54 and 55 serve as reference electrodes. The combination of electrodes provides two cells for the probe, and for purposes of further explaining the invention, cell 1 will be considered to include electrode 51 as the working electrode, electrode 50 as the counter electrode, and electrode 55 as the reference electrode; while cell 2 would have the electrode 50 serving as the working electrode, the electrode 51 serving as the counter electrode, and the electrode 54 serving as the reference electrode. It is important that the reference electrodes be as close as possible to the working electrodes to minimize electronic errors in the measurement. As seen in FIG. 5, the working electrode circuitry is designated 52, while the counter electrode circuitry is designated 53. The reference electrodes include circuitries 56 and 57.

Referring again to FIG. 5, the glassy carbon electrodes 50 and 51 of the probe serve as both working and counter electrodes for the cells, while the silver electrodes 54 and 55 serve as reference electrodes and are positioned as close as possible to the glassy carbon electrodes without touching. The switches 74 of FIG. 7 include switches for the working, counter and reference electrodes to switch between cells during measurements, and which are controlled by the microprocessor programming.

A current measurement for measuring nitrite concentration is taken between the working electrode circuitry at 52a, and the counter electrode circuitry at 56a to measure current flow in the cell. Cell 1 operation involves switching the working electrode circuitry 52 to connect to contact 51b of electrode 51 making it the working electrode, connecting the counter electrode circuitry 53 through contact 50b to make electrode 50 the counter electrode and connecting the input 56a of the reference electrode through contact 55a to electrode 55, which is closest to the working electrode 51 of this cell. The reference electrode fixes the potential of the working electrode when current is passing through the cell. Ramping the potential of the working electrode is done by application of the potential $E_i$ between the working and reference electrodes. Thus, current flow through the cell and through the working and counter electrodes is only determined by nitrite concentration as long as the working potential is fixed at a known value. During operation of cell 2 the switches connect the working electrode circuitry 52 through the contact 51a to the electrode 50 of the probe, connect the counter electrode circuitry 53 to the contact 50a and the electrode 51 of the probe, and connect the reference electrode line 56a to the reference electrode 54 through contact 54a. Again, the reference electrode fixes the potential of the working electrode when current is passing through the cell.

The temperature compensation sensor 58 is suitably located below the outer surface of the probe, as shown in FIGS. 2 and 3, while also being at one side of the cavity in which the electrodes are supported. Its location should be substantially equidistant from the other electrodes. Epoxy also supports the temperature sensor in relation to the electrodes.

The conductors for the electrodes, the temperature sensor, and the ground are also supported within the cavity of the probe casing by the potting compound and then are brought together with an outer insulating cover and extended from the tail end of the casing as the probe lead 64 which is then connected into the analyzer 35. The leads to the electrodes, temperature sensor and the ground are suitably insulated from each other in a known manner.

Each cell of the probe 30 functions in the form of a three electrode potentiostat as electrically schematically shown in FIG. 5 in a well known manner, so as to oxidize nitrite in the water and measure the current flow to provide a measurement commensurate with the nitrite concentration. Each electrochemical cell includes a working electrode, a counter electrode, and a reference electrode, as above described, and the current flow between the working electrode and counter electrode is measured.

Figure 6:
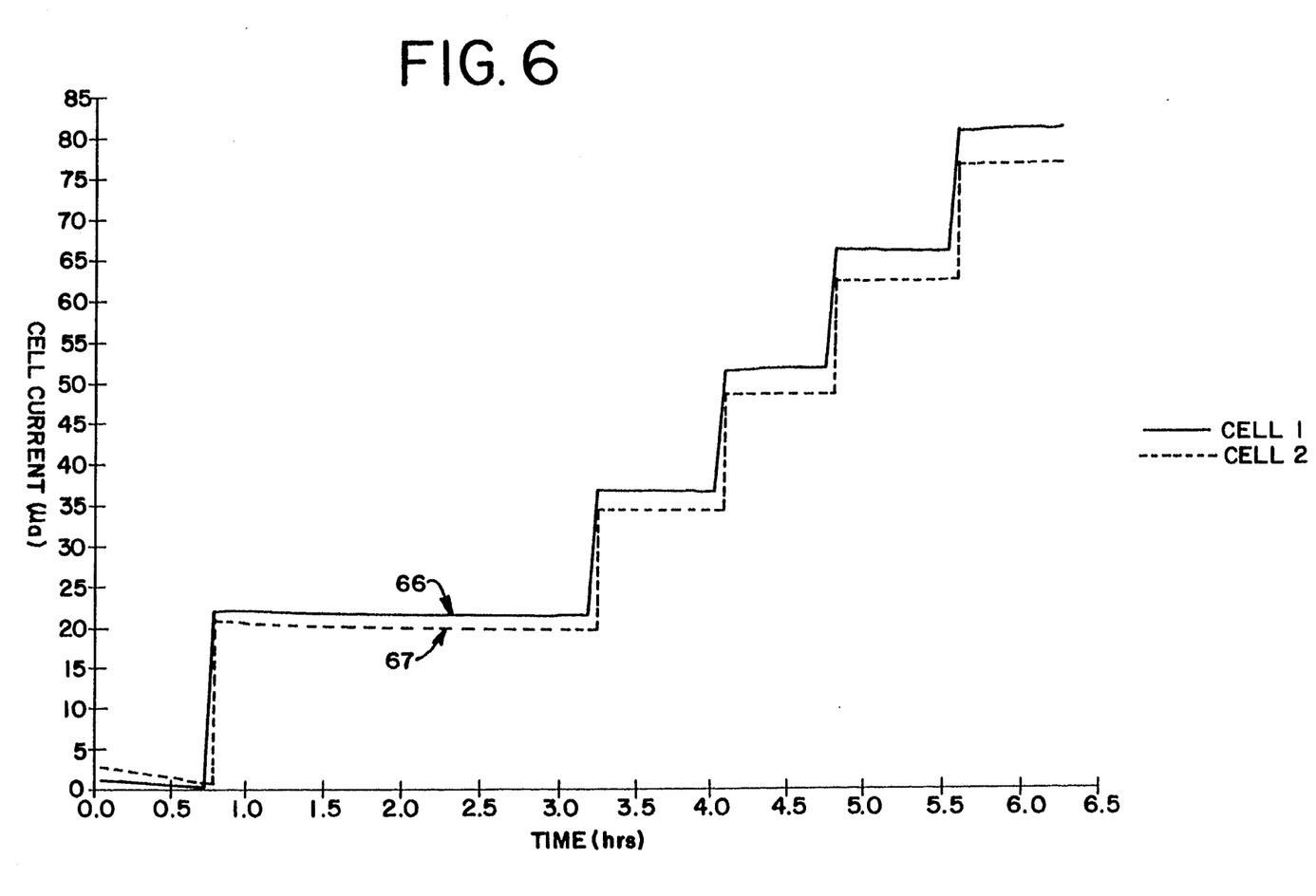
FIG. 6 is a graphical illustration of the probe operation at various nitrite levels.

In order to illustrate probe operation, the probe was immersed in an aqueous solution at various nitrite concentrations, and measurements were taken at the various levels. This test showed that the probe response was different at known amounts of nitrite concentrations, thereby showing the reproducibility of readings and the stability at any one level. This test also showed the sensitivity of the probe and that the calibration curve would be linear. The test is illustrated in the graph of FIG. 6 where the test was made over a period of 6.5 hours and measurements were taken from each cell. The solid line 66 represents the measurements taken from cell 1, while the dotted line 67 represents the measurements taken from cell 2. This information is used to construct the calibration curve used by the microprocessor.

The aqueous solution initially contained no nitrite, and measurements were taken over a period of about 45 minutes, which produced substantially no current measured. Nitrite was periodically added at the rate of 100 ppm. Thus, each step up along the curve represents the addition of an additional 100 ppm of nitrite. The first step shows a measurement of between 20 and 25 microamps, which remained stable over a period of about three hours.

The next step up shows a current reading of between 35 and 40 microamps over a period of about one hour. Adding nitrite to increase the concentration another 100 ppm showed the next step to increase the current readings to about 50 microamps and thereafter sequentially to about 65 microamps and 75 microamps at one hour intervals. As above noted, this test operation illustrates the calibration curve to be linear, that over time the reproducibility of readings would be stable, the response of the probe would be different for known amounts of nitrite, and that the probe responds in a controlled manner.

Figure 7:
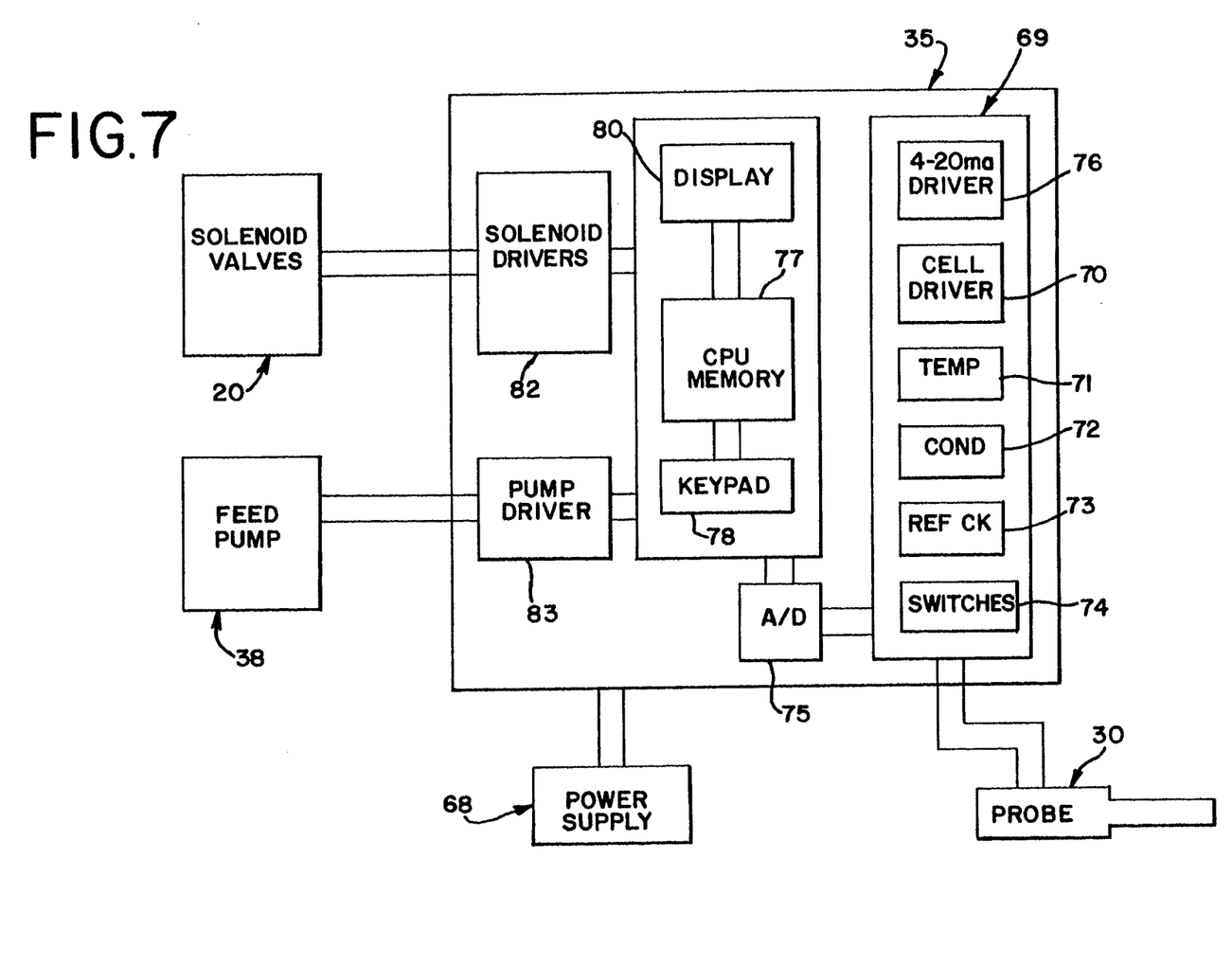
FIG. 7 is a block diagram of the overall system of the apparatus for monitoring and controlling chemical concentration according to the present invention.

Referring now to FIG. 7, a block diagram of the invention is shown wherein the sensor connects into the analyzer 35 which also includes outputs for the solenoid valve 20 and the feed pump 38. A power supply 68 is shown to provide power to the electronic components and the sensor. As above mentioned, a power supply check is made during each cycle when a measurement and calculations are made. A cell driver 70 provides the potential levels for the electrodes of the sensor 30. A temperature measurement is made by the electronic components 71 through the temperature sensor 58 in the probe 30. A conductivity check is made by the conductivity component 72, while a reference check is made by the reference check component 73. The switches component 74 provides the switching between various checks and measurements of the cells. The analog measurements of the components 71 to 73 are converted into a digital signal by the analog-to-digital converter 75. Ahead of the converter 75 is a 4–20 milliamp driver 76 to which may be connected a chart recorder, a data log system, or a pump control unit.

The digital signal from the A/D converter 75 is received by the microprocessor which is combined with a memory in block 77. The memory of the block maintains the calibration curve and the sequence of events which are used to control operation of the probe 30, all of which are programmed in any suitable computer language as is well known by a programmer. An acceptable microprocessor would be an 80C52 unit, currently sold by Harris Semiconductor, Inc., although other microprocessors or other collections of memory, registers, counter timers and an arithmetic logic unit providing equivalent functions could be used. The details and operation of an 80C52 microprocessor are known to those skilled in the art of microprocessors. A 16-key keypad 78 is connected to the microprocessor to input the memory for adjusting the calibration curve. An alpha-numeric display 80 is connected to the microprocessor for displaying the nitrite level, temperature, conductivity, and any other suitable information desired. A solenoid driver 82 receives a signal from the microprocessor to energize or de-energize the solenoid of the solenoid valve 20. Further, a pump driver 83 receives a signal from the microprocessor to either turn the feed pump 38 on or off.

Figure 8:
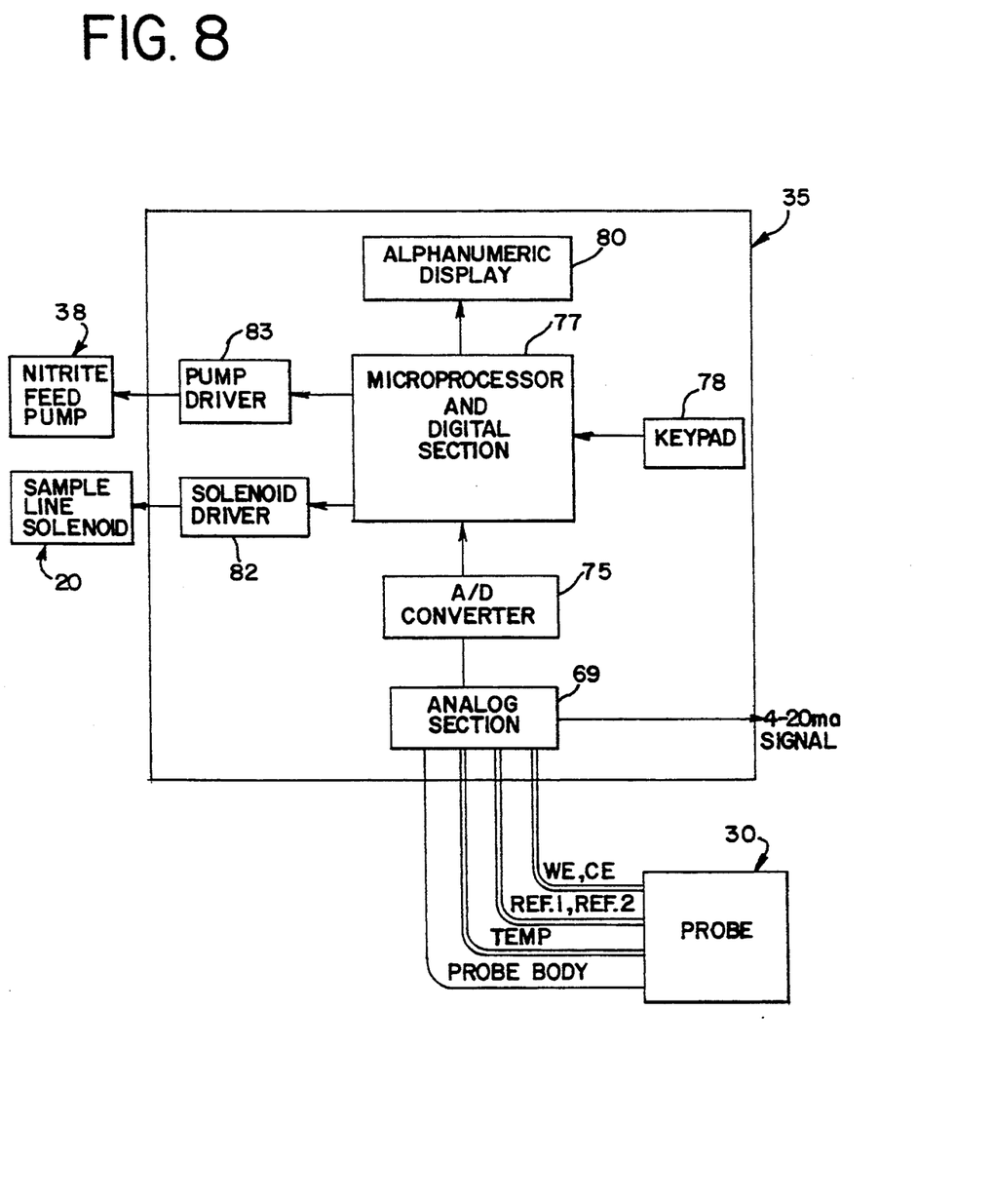
FIG. 8 is a flow diagram of the apparatus of the present invention.

As shown in the flow diagram in FIG. 8, the probe 30 is connected to the analog section 69 which is in turn connected to the A/D converter 75 that is in turn connected to the microprocessor and digital section 77. The analog signals generated by the probe converted to digital signals by the A/D converter, are fed to the microprocessor. After processing the inputs, the microprocessor formulates commands to the pump driver 83 and the solenoid driver 82 for respectively controlling the operation of the nitrite feed pump 38 and the sample line solenoid 20.

Figure 9:
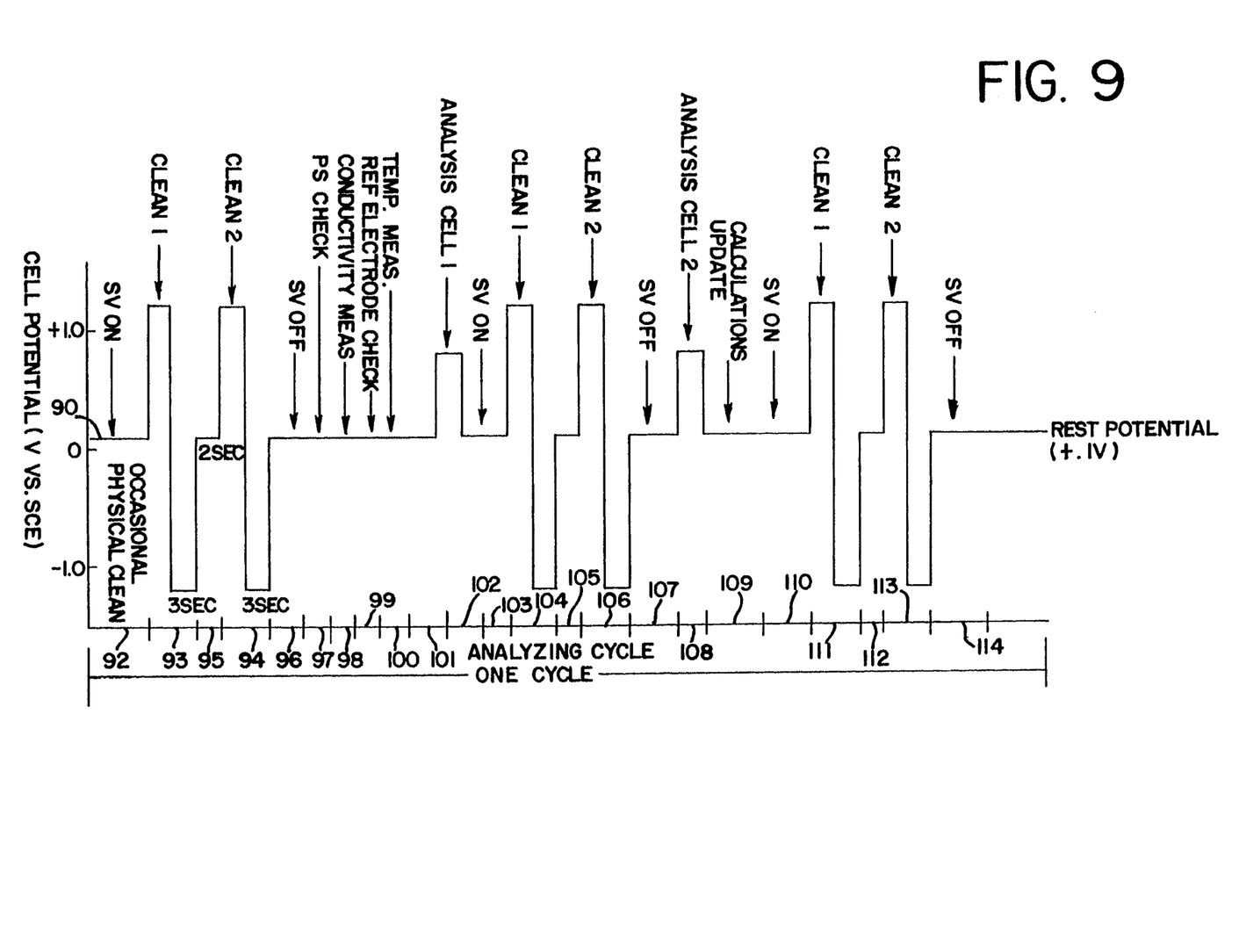
FIG. 9 is a graphical illustration of a timing chart illustrating the operation of the analyzing cycle of the apparatus of the present invention.

Referring now to the timing diagram of the analyzer in FIG. 9, the programmed analyzing cycle is illustrated, which consumes about one minute of time where a nitrite concentration measurement is made about every four to five minutes. Thus, a time period of about four to five minutes will be programmed by the microprocessor between nitrite concentration measurements and the measurement cycle of the analyzer, although this time period may be adjusted for any system. As above mentioned, during the intervals between measurements, the glassy carbon electrodes will be subjected to a continuous cleaning mode wherein alternating positive and negative voltage potentials of about 1.2 volts will be applied to these electrodes. The cell potential is plotted on the vertical axis and time on the horizontal. The rest potential for the cells is a positive 0.1 volt between the working electrode and reference electrode and is illustrated by line 90 at the beginning of the cycle, intermediate points along the cycle when certain operations take place, and at the end of the cycle. Segments on the horizontal axis of this graph will be hereafter identified in connection with functions during the cycle. The solenoid valve 20 is turned on by the microprocessor through the solenoid driver 82 at function 92 to provide sample flowing past the probe 30 and for flushing the sample line. During the time that the solenoid valve is on and sample is flowing past the probe, first cell 1 is cleaned by function 93 and then cell 2 is cleaned by function 94. During each of these cleaning cycles to maintain the electrode surfaces clean to obtain accurate measurements, the cells are subjected to positive and negative voltage potentials between the respective reference and working electrodes of about 1.2 volts for about three seconds each. A two-second interval function 95 between cell cleaning modes is provided to switch from cell 1 to cell 2. The potentials applied are between the glassy carbon electrodes. Following the cleaning of the cells, the solenoid valve is turned off at function 96 so as to render the sample stationary for the nitrite concentration measurement.

Successively before the nitrite level measurement, the analyzer steps through function 97 to check the power supply, function 98 to check the conductivity of the sample, function 99 to check the potential of the reference electrodes which must be essentially zero, and function 100 to check the temperature of the sample, all while the probe is at rest potential. The reference electrodes, being silver-coated with silver chloride or a mixture of silver chloride and silver sulphide, sense the chloride concentration naturally in the water to make the reference check. If the power supply output is inadequate, the measuring cycle will be aborted. The conductivity of the sample must be within a window or range, and if not, a hydrogen blast or gas evolution cleaning of the carbon electrodes will be conducted where the probe body is grounded and a potential is applied between the probe body and the carbon electrodes, causing high hydrogen gas evolution at the carbon electrodes that can remove physically attached debris. The conductivity check is performed by applying a 300 Hz+0.3 V peak-to-peak potential to the glassy carbon electrodes and measuring the current value which is proportional to the conductivity of the sample. This check determines if a sample is present, the value which must be at a minimum that relates to the nitrite level, and applies a correction factor for the measurement of nitrite concentration.

More particularly, the above physical cleaning of the glassy carbon electrodes 50 and 51 of the probe 30 may be accomplished in one or two steps. For example, the potential may be applied between the casing 45 and one or both of the glassy carbon electrodes 50 and 51 at the same time. Only a positive potential is applied, and it may be applied between one glassy carbon electrode functioning as a counter electrode and the casing functioning as a working electrode and then the other glassy carbon electrode functioning as a counter electrode and the casing functioning as a working electrode.

Also, the microprocessor may be programmed to regularly cycle through a physical cleaning mode of the glassy carbon electrodes. Normally, it will be sufficient to do this every 24 hours, but it could be done at any desired interval.

If the reference check which constitutes measuring the potential between the reference electrodes is not substantially at zero as it should be, the nitrite concentration measurement will not be made and an error will show on the display.

During the temperature measurement function 100, a plurality of readings will be taken and averaged. For example, ten readings of the temperature may be taken and averaged for the purpose of temperature compensating the cell current measurements.

Each of the functions 97, 98, 99 and 100 will take one or two seconds, and a short one or two second function 101 follows the checks prior to conducting a measurement of nitrite concentration current of the cells. During each of these functions except the conductivity check 98, the probe cells are at rest potential.

As above stated, the conductivity check is made to determine the presence of a sample, that a minimum value relating to nitrite concentration is present, and as a correction factor when cell current is measured for nitrite concentration. During the conductivity check a 300 hz+0.3 V peak-to-peak potential is applied to the cell.

If all checks are acceptable, the microprocessor causes cell 1 to operate to take a current measurement commensurate with the nitrite concentration level by going through function 102. The measuring step includes ramping up the voltage at the reference electrode from +0.1 to +0.7 volts, holding the potential at +0.7 volts for about three seconds and then taking a current measurement between the working and counter electrodes just before the voltage is dropped. This current measurement is converted to a nitrite concentration by the microprocessor in accordance with the calibration curve stored in memory and held for the measurement of the second cell for averaging purposes and before being transmitted to the display. The cells are then switched and a further current measurement is taken. Prior to that measurement, the microprocessor causes the solenoid valve 20 to turn on by function 103 to flush the sample, and during the time the solenoid valve is on, cell 1 will be operated to go through a cleaning mode by function 104. The cells will be switched by function 105 and cell 2 will be subjected to a cleaning mode by function 106. The solenoid valve is then turned off by function 107, and the microprocessor then switches the analyzer to conduct the measurement of cell 2, while the cells are at rest potential. The potential in cell 2 is then ramped up to +0.7 volts by function 108 and held for about three seconds, and just before the potential drops off, a current measurement is made. The microprocessor then goes through function 109 for calculating the measurement to be used for reading out the nitrite concentration. Compensation is performed for each cell when the current measurement is taken where it is corrected for temperature and conductivity; the nitrite concentration will be based on the calibration curve in the memory of the microprocessor. The calculations of cells 1 and 2 are averaged to provide a readout in the display 80 of the concentration of the nitrite.

Also, during function 109 a calculation update function will be made for calculating temperature, conductivity and converting current to nitrite, outputting of the 4–20 milliamp via driver 76, displaying new values, and adjusting the pump control if necessary. Thereafter, the solenoid valve is again turned on by function 110, after which cell 1 is cleaned by function 111. The cells are switched by function 112, and cell 2 is cleaned by function 113. The solenoid valve is then turned off by function 114 and the probe is subjected to its continuous cleaning mode until the next analyzing cycle.

The feed pump will be turned on or off depending on the nitrite concentration, as previously explained. The display is updated after each analyzing cycle during the function 109 to display nitrite concentration, the temperature measurement of the sample, and the conductivity measurement of the sample, and whatever other information may be desired. Also, the 4-20 milliamp signal will be updated.

As a further example of the probe measurements, if cell 1 measured the nitrite concentration at 100 ppm and cell 2 measured it at 104 ppm, the average of the cells of 102 ppm would represent a much more reliable reading to control nitrite feeding. Further, if the conductivity measurement is too low relative to the nitrite concentration, the system will not be working properly and an error message would appear on the display. For example, if the sodium nitrite concentration level were 100 ppm and the conductivity measurement was 100 $\mu S$, something would not be working properly. However, if the concentration level was 100 ppm and the conductivity was about 1000 $\mu S$, it would indicate that the system is working properly.

It can now be appreciated that the present invention provides an automated monitoring and feeding system that minimizes the need for frequent maintenance and vigilance by virtue of utilizing an electrochemical process that is automated to monitor and control the nitrite concentration in a water system. Thus, long-term accuracy is accomplished with the present invention without the need for frequent calibration or cleaning, without the need for providing chemical reagents, and by utilizing a minimum number of mechanical parts. Because the probe is operated in a cleaning mode between measurements, it is resistant to fouling. This minimizes maintenance, and because of the minimum number of mechanical parts a high degree of reliability is produced by the present invention.

It will be understood that modifications and variations may be effected without departing from the scope of the novel concepts of the present invention, but it is understood that this application is to be limited only by the scope of the appended claims.

The invention is hereby claimed as follows:

1. An apparatus for electrochemically monitoring and controlling oxidizing or reducing agent concentrations in a water system comprising:
    an inline mounted probe exposed to a water sample of the system, said probe including a plurality of current measuring cells each of which includes a working electrode, a counter electrode and a reference electrode,
    a source of oxidizing or reducing agent, means for selectively feeding the agent to the system,
    and an analyzer and controller connected to the probe for operating the probe and measuring agent concentration by processing the current measured during a measurement cycle, said analyzer being connected to the feeding means for operating the feeding means.

2. The apparatus of claim 1, wherein said analyzer and controller includes means for switching the probe between cleaning and measuring modes and causing said feeding means to operate between feed and non-feed modes in relation to a set point of agent concentration.

3. The apparatus of claim 2, which further includes means selectively maintaining the water sample isolated from said water system at least during the measuring mode.

4. The apparatus of claim 3, wherein said isolation means includes a remotely operated valve driven by the analyzer and controller.

5. The apparatus of claim 4, wherein said means for selectively feeding the agent includes a feed pump, and said analyzer and controller having means to turn the pump on or off depending on the agent concentration in said water system.

6. The apparatus of claim 5, wherein said probe includes two cells, and said analyzer and controller operates the cells to each, takes a measurement and average, the measurements thereby providing a reliable agent concentration measurement for controlling the feed pump.

7. The apparatus of claim 3, wherein said isolation means includes a solenoid valve driven by the analyzer and controller.

8. The apparatus of claim 5, wherein said analyzer and controller includes a microprocessor programmed to operate the probe, the solenoid valve and the feed pump to maintain the optimum agent concentration in the water system.

9. The apparatus of claim 8, wherein said analyzer and controller further includes means to measure and compensate for the temperature of the sample.

10. The apparatus of claim 9, wherein said analyzer and controller further includes means for checking conductivity of the sample to determine if it is reasonably related to the agent concentration.

11. The apparatus of claim 10, wherein said analyzer and controller further includes means for making a reference electrode check.

12. The apparatus of claim 1, wherein the water system is closed.

13. The apparatus of claim 1, wherein the water system is open.

14. In a recirculating water system having a concentration of nitrite, an apparatus for electrochemically measuring and controlling the concentration of nitrite in said recirculating water cooling system to minimize corrosion of steel surfaces of lines and recirculating equipment, said apparatus comprising:
    a sample line connected to a system line for receiving a water sample,
    a probe mounted in the sample line,
    valve means between the probe and the system line for statically conditioning a sample during the measuring of the concentration in the sample,
    a feed pump connected to a supply of nitrite and the system line for selectively feeding nitrite to the water cooling system,
    and analyzer means connected to the probe for operating the probe, the valve means and the feed pump to maintain the nitrite concentration within a set range.

15. The apparatus of claim 14, wherein said probe includes a steel casing, a plurality of electrodes mounted in the casing and electrically insulated from each other, and a temperature sensor.

16. The apparatus of claim 15, wherein said electrodes include a plurality of electrodes of non-reactive electrically conductive material and a plurality of silver-based reference electrodes.

17. The apparatus of claim 16, wherein said electrodes of non-reactive electrically conductive material are glassy carbon.

18. The apparatus of claim 16, wherein said electrodes of non-reactive electrically conductive material are a noble metal.

19. The apparatus of claim 16, wherein said silver-based electrodes include a silver base coated with silver chloride.

20. The apparatus of claim 16, wherein said silver-based electrodes include a silver base coated with a mixture of silver sulphide and silver chloride.

21. The apparatus of claim 16, wherein said electrodes are connected to said analyzer means and operated as a plurality of measuring cells.

22. The apparatus of claim 21, wherein each cell includes a working electrode, a counter electrode and a reference electrode.

23. The apparatus of claim 22, wherein said electrodes include a pair of glassy carbon electrodes and a pair of silver-based electrodes, each glassy carbon electrode being proximate to a silver-based electrode.

24. The apparatus of claim 23, wherein said analyzer means includes means operating said electrodes as a pair of nitrite concentration measuring cells, each cell consisting of a working electrode, a counter electrode and a reference electrode, said glassy carbon electrodes operating as working and counter electrodes, and said silver-based electrodes operating as reference electrodes.

25. The apparatus of claim 24, wherein said analyzer means further includes means for driving said probe in a cleaning mode by cycling the glassy carbon electrodes between positive and negative voltage potentials to cause cleaning of the electrodes, and in a nitrite concentration measuring mode by applying a positive potential to a cell to oxidize the nitrite in the sample and measure the current in the cell and convert the current measurement to a ppm nitrite concentration level.

26. The apparatus of claim 25, wherein said analyzer means further includes means for driving said probe in a physical cleaning mode on at least a daily basis by applying a potential between the steel casing and the glassy carbon electrodes.

27. The apparatus of claim 25, wherein said means for driving the electrodes in said measuring mode further includes opening said valve means to allow sample to flow past the probe to drain, subjecting the cells to a cleaning operation, closing said valve means to statically condition the sample, checking the power supply, checking the conductivity of the sample, conducting a reference electrode check, and making a temperature measurement, all prior to measuring the current in the cells.

28. The apparatus of claim 27, wherein said analyzer means further includes means for averaging the concentration measurements of each cell, and means for turning the feed pump on or off depending on the set point for the nitrite concentration.

29. The apparatus of claim 28, wherein said analyzer means further includes means for discontinuing the measuring mode if the conductivity measurement of the sample is outside a set range.

30. The apparatus of claim 21, wherein said glassy carbon electrodes include a circularly shaped flat surface exposed to the sample, and said silver-based electrodes include a semi-tubular shaped flat surface exposed to the sample, one each arranged in closely spaced concentric relation to a glassy carbon electrode.

31. A method of electrochemically measuring and controlling the concentration of nitrite in a recirculating water cooling system to minimize corrosion of steel surfaces of lines and/or recirculating equipment which comprises the steps of:

providing a sample line to receive a water sample from the system to measure the nitrite concentration, providing means for selectively supplying nitrite to the system, providing a probe in the sample line, wherein the probe includes a plurality of nitrite concentration electrochemical measuring cells, each of which includes a plurality of electrodes, providing a power supply for said cells, operating the probe to maintain the electrodes clean for taking optimum concentration measurements, statically conditioning the sample, supplying a voltage potential to the cells, measuring the current through the cell, converting the current measurement to a nitrite concentration, and driving the nitrite supplying means in accordance with a set point of the measured concentration of nitrite.

32. The method of claim 31, which prior to the current measurement step further includes the steps of providing a fresh sample of cooling water to the probe during the current measuring step of each cell.

33. The method of claim 32, wherein said probe includes a pair of glassy carbon electrodes, a pair of silver-based electrodes and a temperature sensor, and said method further includes the steps of operating said electrodes as a pair of nitrite concentration measuring cells, each cell consisting of a working electrode, a counter electrode and a reference electrode, said glassy carbon electrodes operating as working and counter electrodes, and said silver-based electrodes operating as reference electrodes.

34. The method of claim 33, which further includes ramping up the voltage potential of each cell to oxidize nitrite and measuring current across the working and counter electrodes just prior to dropping the potential.

35. The method of claim 34, which prior to the current measurement step of each cell further includes the steps of providing a fresh sample to the probe, subjecting the cells to a cleaning operation, checking the power supply, checking the conductivity of the sample, conducting a reference electrode check, and taking a temperature measurement of the sample through the sensor in the probe.

36. The method of claim 35, which further includes the step of physically cleaning the electrodes at least once daily by applying a potential between the probe casing and the glassy carbon electrodes.

37. The method of claim 36, which further includes the step of discontinuing the operation of the probe to make a nitrite concentration current measurement if the conductivity check is outside a set range.

38. An apparatus for electrochemically monitoring oxidizing or reducing agent concentrations in a water system comprising:

an inline mounted probe exposed to a water sample of the system, said probe including a plurality of current measuring cells each of which includes a working electrode, a counter electrode and a reference electrode, and an analyzer connected to the probe for operating the probe and measuring agent concentration by processing the current measured during a measurement cycle.

39. The apparatus of claim 38, wherein said analyzer further including means for switching the probe between cleaning and measuring modes.

40. A method of electrochemically measuring and controlling the concentration of nitrite in a recirculating water cooling system to minimize corrosion of steel surfaces of lines and/or recirculating equipment which comprises the steps of:

provide a sample line to receive a water sample from the system to measure the nitrite concentration, providing a probe in the sample line, wherein the probe includes a plurality of nitrite concentration electrochemical measuring cells, each of which includes a plurality of electrodes, operating the probe to maintain the electrodes clean for taking optimum concentration measurements, statically conditioning the sample, measuring the current through the cell, converting the current measurement to a nitrite concentration.

* * * * *